(12) United States Patent
Bohl et al.

(10) Patent No.: US 12,635,847 B2
(45) Date of Patent: May 26, 2026

(54) SYSTEM AND METHOD FOR FORCE ESTIMATION APPLIED TO ENDOSCOPES

(71) Applicant: Arthrex, Inc., Naples, FL (US)

(72) Inventors: Andrew Bohl, Santa Barbara, CA (US); John Hygelund, Santa Barbara, CA (US)

(73) Assignee: Arthrex, Inc., Naples, FL (US)

( * ) Notice: Subject to any disclaimer, the term of this patent is extended or adjusted under 35 U.S.C. 154(b) by 70 days.

(21) Appl. No.: 18/524,348

(22) Filed: Nov. 30, 2023

(65) Prior Publication Data

US 2024/0180394 A1     Jun. 6, 2024

Related U.S. Application Data

(60) Provisional application No. 63/429,620, filed on Dec. 2, 2022.

(51) Int. Cl.
*A61B 1/00* (2006.01)
*A61B 1/04* (2006.01)

(52) U.S. Cl.
CPC ...... *A61B 1/00009* (2013.01); *A61B 1/00006* (2013.01); *A61B 1/041* (2013.01)

(58) Field of Classification Search
CPC . A61B 1/00009; A61B 1/00006; A61B 1/041; A61B 1/042
See application file for complete search history.

(56) References Cited

U.S. PATENT DOCUMENTS

| | | | |
|---|---|---|---|
| 5,060,632 A * | 10/1991 | Hibino | A61B 1/00042 |
| | | | 600/109 |
| 7,245,412 B2 | 7/2007 | Bruland et al. | |
| 7,833,018 B2 | 11/2010 | Alexander et al. | |
| 7,931,588 B2 * | 4/2011 | Sarvazyan | A61B 1/31 |
| | | | 600/117 |
| 8,373,748 B2 | 2/2013 | Pang et al. | |
| 9,060,674 B2 | 6/2015 | Amling | |
| 10,722,102 B2 | 7/2020 | Hygelund et al. | |
| 10,736,494 B2 * | 8/2020 | Gora | A61B 5/0066 |
| 10,791,908 B2 * | 10/2020 | Au | A61B 1/009 |
| 11,166,623 B2 * | 11/2021 | Steiner | A61B 1/045 |
| 2008/0146875 A1 | 6/2008 | Noguchi et al. | |
| 2010/0049033 A1 * | 2/2010 | Kawano | A61B 5/06 |
| | | | 600/117 |
| 2013/0304446 A1 * | 11/2013 | Rabinovitz | A61B 1/00158 |
| | | | 703/11 |

(Continued)

FOREIGN PATENT DOCUMENTS

EP          1844696 A1     10/2007

*Primary Examiner* — Timothy R Newlin

(74) *Attorney, Agent, or Firm* — Price Heneveld LLP

(57) ABSTRACT

A surgical imaging apparatus includes an imager configured to capture image data in a field of view and an elongated probe extending from a proximal end to a distal end. The distal end has a distal window through which the field of view is aligned. A controller is in communication with the imager and configured to detect a feature in the image data and identify a feature location of the feature in the image data. The controller further monitors the feature location in the image data. In response to a change in the feature location from a first position to a second position, the controller calculates an estimated force applied to the elongated probe.

20 Claims, 7 Drawing Sheets

(56)                    References Cited

U.S. PATENT DOCUMENTS

| | | | | |
|---|---|---|---|---|
| 2014/0107415 A1* | 4/2014 | Amling | ................. | A61B 1/045 |
| | | | | 600/109 |
| 2014/0276022 A1 | 9/2014 | Oghalai et al. | | |
| 2015/0099925 A1* | 4/2015 | Davidson | ................. | A61B 1/04 |
| | | | | 600/117 |
| 2015/0208947 A1* | 7/2015 | Tojo | ....................... | A61B 1/009 |
| | | | | 600/104 |
| 2017/0027417 A1* | 2/2017 | Kawai | ................ | A61B 1/00154 |
| 2018/0325607 A1* | 11/2018 | Isoda | ................. | A61B 1/00149 |
| 2019/0058819 A1 | 2/2019 | Kobayashi | | |
| 2020/0015902 A1* | 1/2020 | Scheib | ..................... | A61B 1/05 |
| 2021/0169314 A1* | 6/2021 | Tsai | ................. | A61B 1/00078 |
| 2021/0236773 A1* | 8/2021 | Dupont | ........... | A61B 1/000096 |
| 2022/0022948 A1* | 1/2022 | Fujii | ........................ | A61B 1/05 |
| 2022/0039658 A1* | 2/2022 | Smith | ............... | G01B 9/02025 |
| 2025/0097559 A1* | 3/2025 | Murakita | ............. | H04N 23/675 |

* cited by examiner

SYSTEM AND METHOD FOR FORCE ESTIMATION APPLIED TO ENDOSCOPES

CROSS-REFERENCE TO RELATED APPLICATIONS

This application claims priority under 35 U.S.C. § 119(e) and the benefit of U.S. Provisional Application No. 63/429, 620 entitled SYSTEM AND METHOD FOR FORCE ESTIMATION APPLIED TO ENDOSCOPES, filed on Dec. 2, 2022, by Bohl et al., the entire disclosure of which is incorporated herein by reference.

BACKGROUND

The present disclosure generally relates to endoscopes or scopes used in surgery and, more particularly, to video scopes or similar instruments configured to detect applied forces during operation. In many cases, endoscopes or video scopes applied for surgical applications may be subjected to harsh environments and considerable applied forces that may be necessary to maneuver a field of view to capture image data demonstrating a target region of a patient. The disclosure provides for systems and methods that may be implemented to detect forces applied to endoscopes and similar devices to document and improve their operation in the field.

SUMMARY

The disclosure provides for various methods and related devices for detecting forces applied to endoscopes, arthroscopes, or similar imaging devices to monitor, report, and/or output alerts identifying use events associated with the operation of the devices in the field. In various implementations, the disclosure may provide for a method of force detection that is capable of accurately estimating forces applied to an elongated probe of a surgical imaging device by monitoring the image data captured by an imager of the device. Such force detection and estimation may assist manufacturers and end users in determining the forces to which the devices are exposed in the field in order to document or record use events for tracking purposes. By tracking the use and likely wear associated with the devices in the field, suppliers and end users may better identify preventative maintenance schedules and estimate the expected lifetime or service schedule for the imaging devices.

In some cases, the force estimation associated with the disclosure may be monitored to document usage data as well as trigger notifications or alerts identifying forces that may exceed use thresholds associated with intended loading and use scenarios. For example, an endoscopic imaging device implementing the disclosed methods may output one or more alerts or notifications of forces being applied in excess of a predetermined threshold force or pressure. In such cases, users of the devices may be alerted to extreme use conditions. By leveraging the imaging hardware that may already be associated with such devices, the disclosure may provide for such operation without requiring additional sensors (e.g., force sensitive resistors, load cells, strain gauges, etc.). Accordingly, the disclosure may provide for monitoring, reporting, and improved operation of endoscopes, arthroscopes, laparoscopes, and similar video imaging devices without requiring dedicated sensory hardware.

The disclosure may be implemented with surgical imaging apparatuses that capture image data via a distal viewing window located at a distal end of an elongated probe. In operation, a controller may process the image data captured by the imager in order to detect one or more features and identify corresponding feature locations within a field of view. In some implementations, the controller may further be configured to determine a rotational orientation of the elongated probe relative to the imager based on a datum location of a rotational datum or feature, which also may be identified in the image data. Once identified, the controller may further monitor a feature location of the feature and the datum location of the datum in the image data throughout operation. Based on a detected change in the feature location from a first position to a second position identified in the image data, the controller may generate a force estimate of the applied force acting on the imaging apparatus.

In some examples, the calculation of the force applied to the elongated probe may account for a portion of the change identified in the feature location from the first position to the second position that may be associated with the rotational orientation of the elongated probe. The determination of the rotational orientation of the elongated probe may be particularly beneficial in arthroscopic or laparoscopic application where a field of view is angled or offset from an instrument axis of the elongated probe. In such cases, the force estimate may be improved by isolating a change in the feature position associated with an applied force from a change associated with the rotation of the elongated probe and the related viewing axis. In this way, the disclosure may be flexibly applied to a variety of imaging devices to detect and estimate applied forces.

These and other features, objects and advantages of the present disclosure will become apparent upon reading the following description thereof together with reference to the accompanying drawings.

DETAILED DESCRIPTION

In the following description, reference is made to the accompanying drawings, which show specific implementations that may be practiced. Wherever possible, the same reference numbers will be used throughout the drawings to refer to the same or like parts. It is to be understood that other implementations may be utilized and structural and functional changes may be made without departing from the scope of this disclosure.

Figure 1:
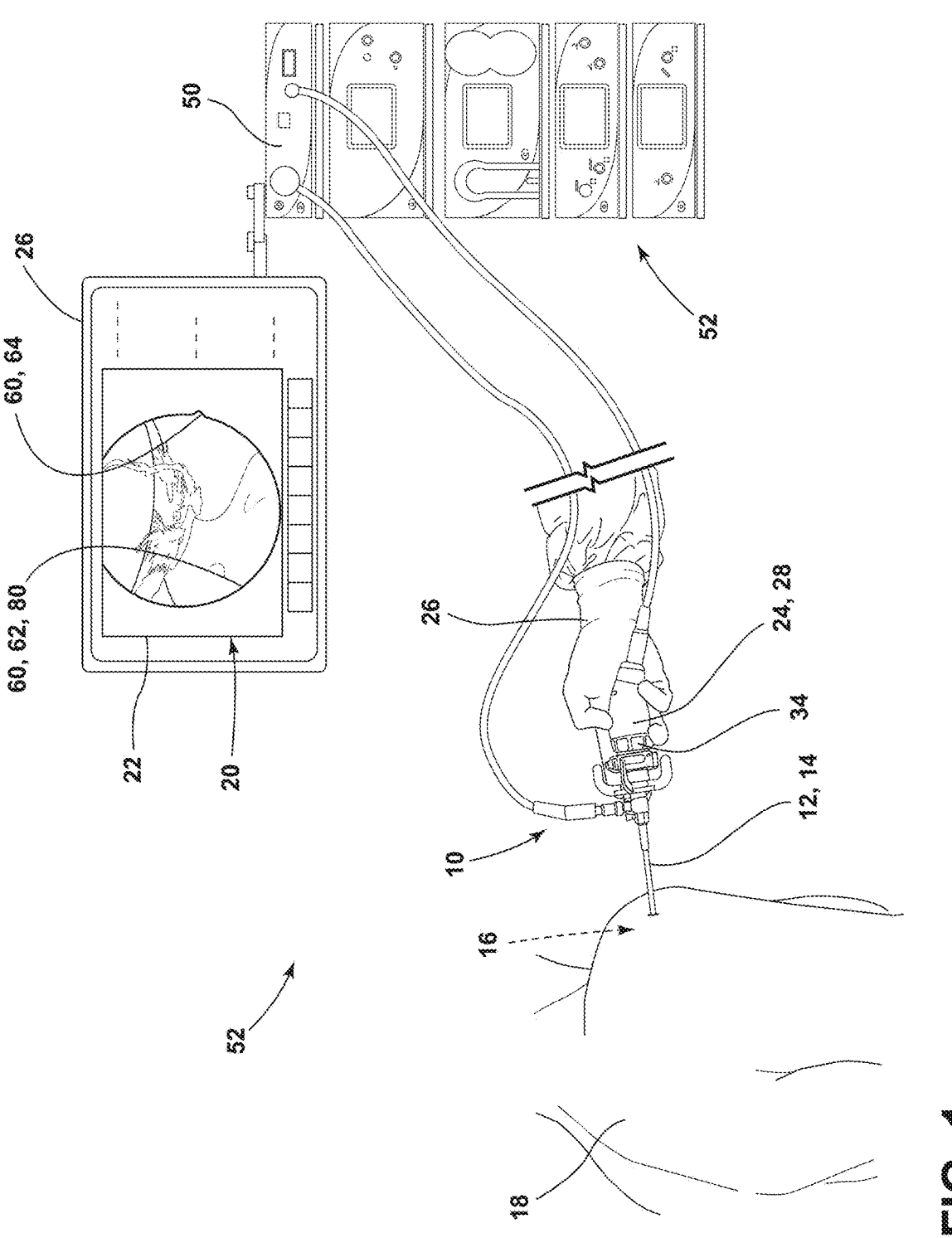
FIG. 1 is an environmental view of a surgical imaging device operating in an exemplary surgical environment.
Figure 2:
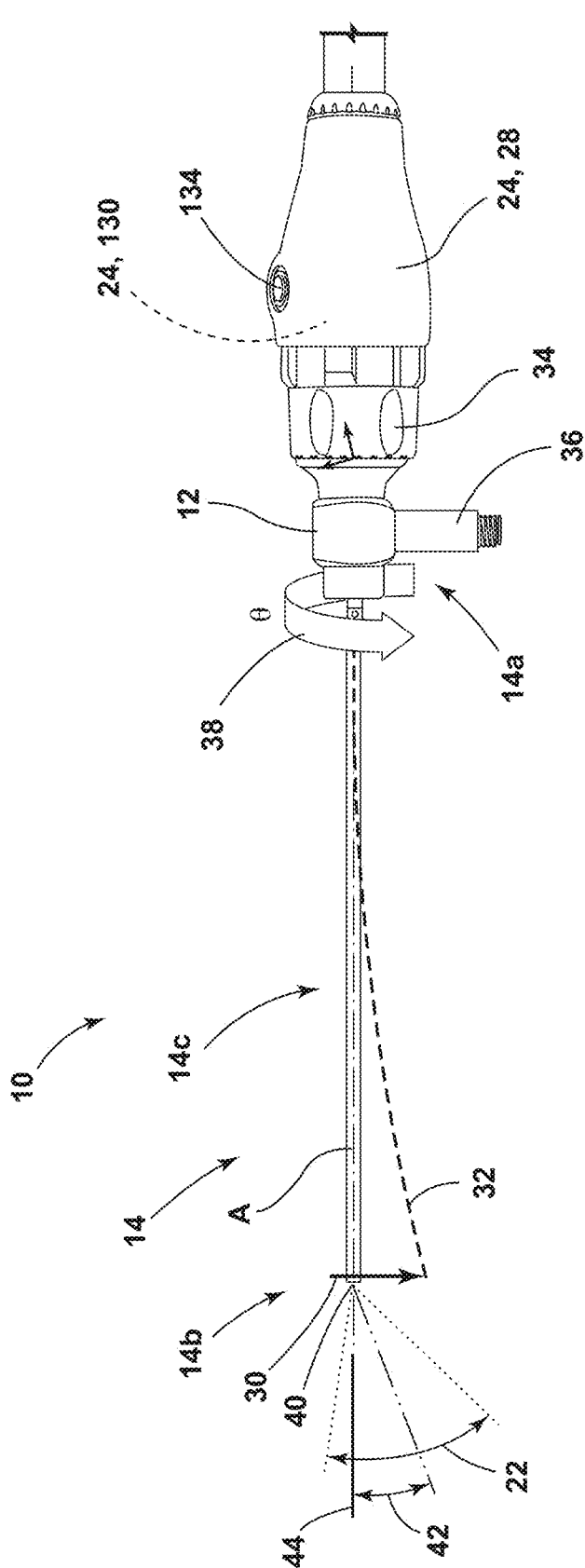
FIG. 2 is a pictorial diagram of an example of an applied force and resulting displacement applied to a surgical imaging device.

Referring now to FIGS. 1 and 2, the disclosure generally provides for a system and method for detecting and estimating forces applied to a variety of surgical imaging devices 10. FIG. 1 demonstrates an example of an imaging device 10 in the form of an arthroscope or endoscope 12 applied in a minimally invasive surgical procedure. During such applications, an elongated probe 14 of the endoscope 12 may be inserted into an operating cavity 16 or joint cavity of a patient 18 to capture image data 20 representing a field of view 22 depicting the operating cavity 16. In operation, an imager 24 or image sensor of the endoscope 12 may be manipulated and moved by a user (e.g., a physician, surgeon, nurse, etc.) to capture portions of the operating cavity 16 within the field of view 22. As shown in FIG. 1, the image data 20 may be displayed on a display device 26 in communication with imaging device 10. Throughout various surgical operations, a camera body 28 connected to a proximal end 14*a* of the elongated probe 14 may be subjected to various applied forces commonly associated with the user adjusting the position and/or orientation of a distal end 14*b* of the elongated probe 14 within the operating cavity 16. Though discussed in reference to an endoscope, it shall be understood that the disclosure may be implemented with various imaging devices that may have the elongated probe 14 susceptible to bending and deflection.

In some cases, the forces applied to the endoscope 12 may be considerable, particularly when maneuvering the elongated probe 14 within rigid joint spaces or cavities within the operating cavity 16. As depicted in FIG. 2, a force diagram is shown demonstrating the endoscope 12 under a simulated load applied to the distal end portion 14*b* of the elongated probe 14. As a result of the applied force (annotated as an arrow 30), a deflection 32 may result along a length 14*c* or working length of the elongated probe 14. As a result of the deflection 32, one or more features in the image data 20 may be shifted or translate within the field of view 22, as discussed later in reference to FIGS. 3 and 4. As described in various examples, the disclosure may provide for the detection of such shifts or translations in features identified in the image data 20 and estimate an amplitude of the applied force 30 in response to an extent (e.g., a pixel distance) of the translation of the features within the field of view 22 of the imager 24. Note that the deflection 32 demonstrated in FIG. 2 may be emphasized to show detail.

As generally discussed throughout the disclosure, the imaging device or apparatus 10 may include the elongated probe 14, which may comprise a shaft, a barrel, a sheath, a coupling, an extension, or various elongated portions that may support a lens or optic assembly of the surgical imaging device 10. In operation, such devices may commonly be utilized to access interior cavities or enclosed spaces via an opening that narrowly accommodates the proportions (e.g., the diameter) of the elongated probe 14. In addition to imaging functions, the imaging device 10 or apparatus may include a variety of features including, but not limited to, one or more aspiration and/or irrigation lumens, surgical accessories, graspers, surgical tools or accessories, etc. that may facilitate a wide variety of surgical procedures or operations. Accordingly, the imaging devices 10 and corresponding methods discussed herein may be employed in a number of surgical environments including open or closed air or semi-dry environments (e.g., an insufflated cavity or organ) and fluid immersion environments (e.g., a fluid distended cavity). While the features and operation of imaging devices or apparatuses 10 employed in such environments may vary significantly, the methods of force detection and estimation discussed herein may be modified and applied in a wide variety of environments based on the operating principles, detection methods, and calibration techniques described herein.

In various implementations, a light post 36 or light coupling may extend from a proximal end portion 14*a* of the elongated probe 14, which may facilitate the connection of a light guide for one or more light sources configured to illuminate the field of view 22. Additionally, the endoscope 12 may be rotatably coupled to the camera body 28 via a sealed rotational coupling 34 configured to engage an eye shield or proximal end 14*a* of the elongated probe 14. In such configurations, the endoscope 12 may be free to rotate about an instrument axis A extending along the elongated probe 14 from the proximal end 14*a* to the distal end 14*b*. An arrow is shown in FIG. 2 to demonstrate the rotation 38 of the endoscope 12 relative to the camera body 28. The rotation 38 of the endoscope 12 relative to the camera body 28 may be particularly beneficial in cases where a distal viewing window 40 of the elongated probe 14 is configured to have a viewing angle 42 offset from the instrument axis A.

Still referring to FIG. 2, the viewing angle 42 may be defined by an imaging axis 44 defining the rotation or offset of the viewing angle 42 relative to the instrument axis A. Accordingly, the viewing angle 42 may define a trajectory of a principle point PP indicating an optical center of the field of view 22. The optical center of the field of view 22 may also correspond to a center of distortion associated with the optical system of the endoscope 12. In this configuration, the rotation 38 of the endoscope 12 relative to the camera body 28 may adjust a direction of the viewing angle 42 relative to the instrument axis A, thereby adjusting a protected direction of the field of view 22 relative to the distal end 14*b* of the elongated probe 14. In this configuration, the rotation 38 of the endoscope 12 may be adjusted by the user to vary the direction of the field of view 22 relative to the instrument axis A of the endoscope 12 without varying an orientation of the instrument axis A.

Referring still to FIGS. 1 and 2, additional details regarding the detection of one or more features in the image data are described. As demonstrated in FIG. 2, the orientation or projection direction of the field of view 22 may vary, not only in response to the rotational orientation θ but also in response to the deflection 32. Accordingly, in various implementations, the imaging system 52 of the surgical imaging device 10 may detect and account for the rotational orientation θ, as well as the deflection 32, in order to identify the applied force 30. The detection of the rotational orientation θ may be particularly beneficial in applications where the imaging axis 44 is offset from the instrument axis A and/or where viewing angle 42 is not aligned with the instrument axis A. As discussed later in reference to FIGS. 4A-4D, the rotation and orientation θ of the endoscope 12 may be detected by a controller 50 based on one or more features or datums identified in the image data 20. In this way, a controller 50 of the imaging system 52 associated with the surgical imaging device 10 may be configured to detect the rotational orientation of the viewing angle 42 of the endoscope 12 to improve a force estimate of the applied force 30. Further details of the controller 50 and the imaging system 52 are later discussed in reference to FIG. 6.

Figure 3A:
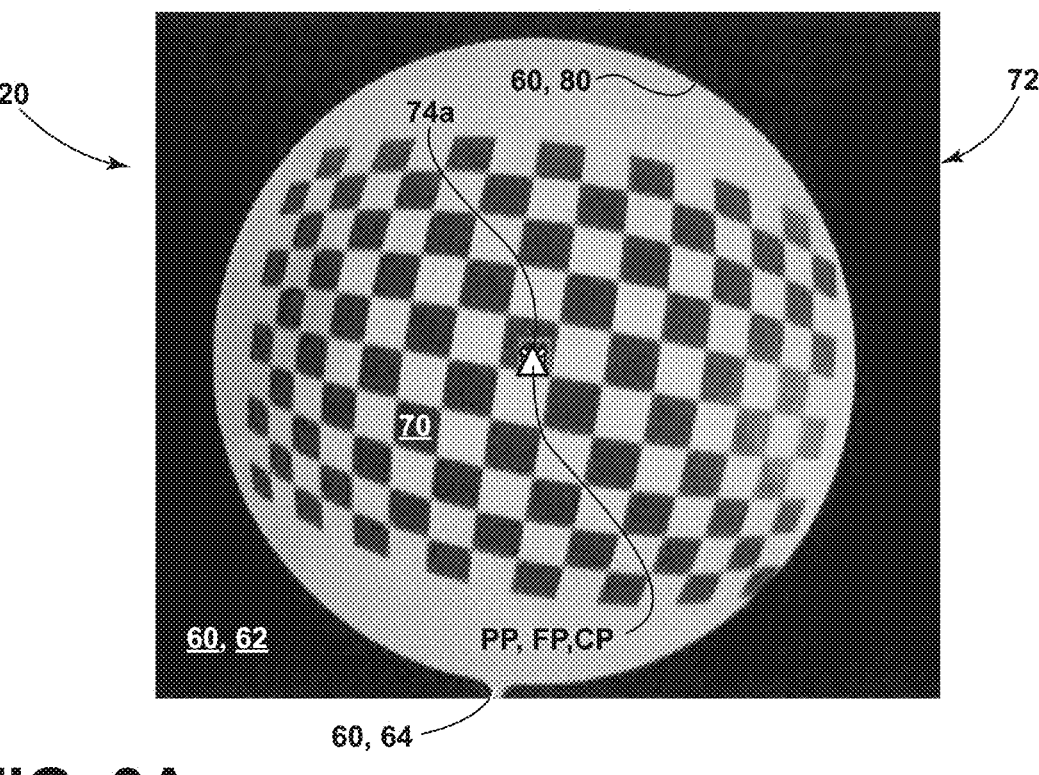
FIG. 3A is a pictorial representation of exemplary image data captured with a surgical imaging device illustrating the position of one or more features present in the image data in response to the device in an undeflected state.
Figure 3B:
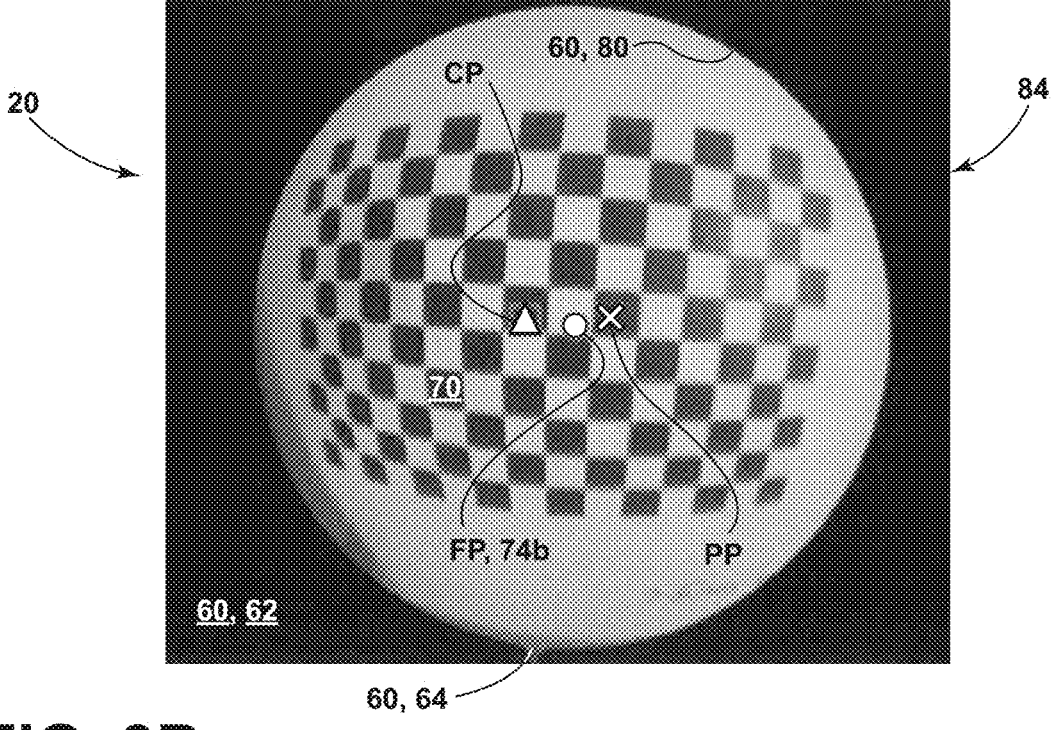
FIG. 3B is pictorial representation of exemplary image data captured with a surgical imaging device illustrating the position of one or more features present in the image data in response to the device in a deflected state.

Referring now to FIGS. 3A and 3B, exemplary features 60 are shown in the image data 20, including a field stop mask 62 and a rotational datum 64 or feature. Though the features 60 are discussed in reference to specific examples, additional features may be detected in the image data 20 to implement the disclosed force estimation. For example, one or more features associated with the field stop mask 62, the optics, the elongated probe 14, and/or various features of the endoscope 12 that may be visible in the image data 20 may similarly be identified and processed by the controller 50. Objects detected in the image data that may similarly be detected and utilized to apply the disclosed force estimate may shift in response to the applied force 30. Accordingly, the imaging system 52 may identify a variety of features 60 in the field of view 22 depicted in the image data 20 to estimate the deflection 32 and the corresponding applied force 30 acting on the elongated probe 14 of the endoscope 12.

As shown in FIGS. 3A and 3B, the image data 20 depicts a checkerboard target 70 that may provide a visual reference and backdrop to illustrate a change in a feature position FP and a principle point PP relative to a center pixel CP in the exemplary image data 20. FIG. 3A demonstrates the image data 20 with the endoscope 12 in an unloaded condition 72. As shown, the endoscope 12 may be assembled and calibrated or otherwise manufactured such that the principle point PP or center of distortion of the optic lens is aligned with the center pixel CP. Additionally, the feature position FP may align with the principle point PP. This feature position FP, the principle point PP, and the center pixel CP may be aligned in the unloaded condition 72 to locate a field center FC of the field stop mask 62 within a perimeter edge 80 of the field stop mask 62. In operation, the unloaded condition 72 may correspond to a first position 74a or a reference position of the feature 60, exemplified as the feature position FP in FIG. 3A. As later discussed in reference to FIG. 3B, the displacement of the feature position FP and/or the principle point PP relative to the center pixel CP demonstrated in the image data 20 may be identified in order to calculate or estimate the magnitude and/or direction of the applied force 30.

In the example shown, the feature 60 is exemplified as the field stop mask 62, and the feature position FP is determined as a field center FC of the field stop mask 62. In operation, the field center FC or center of the field stop mask 62 and the corresponding feature position FP may be calculated by the controller 50 by detecting the perimeter edge 80 in the image data 20. As identified from laboratory and practical testing, the location or feature position FP within the field of view 22 may shift or translate within the image data 20 in correlation with the direction and magnitude of the applied force 30. An example of an exemplary deflection 32 resulting from the applied force 30 is shown in FIG. 3B. Additionally, further details describing examples of a method for identifying the feature position FP as the field center FC, as well as a datum position DP of a datum 64 are discussed in reference to FIGS. 4A-4D.

Referring now to FIG. 3B, the image data 20, including the checkerboard target 70 previously discussed in reference to FIG. 3A, is shown in a loaded condition 84. In the loaded condition 84, the applied force 30 (similar to that discussed previously in reference to FIG. 2) may be applied to a portion of the elongated probe 14, which may be cantilevered from the camera body 28 held by the user. As a result of the applied force 30, the deflection 32 of the elongated probe 14 may cause a change in the feature position FP from the first position 74a to a second position 74b. The change or pixel distance between the first position 74a and the second position 74b may have a direct correspondence to the magnitude of the applied force 30. Additionally, a direction of the applied force 30 may be identified based on a direction of the change between the first position 74a to a second position 74b. Accordingly, the pixel distance or distance between the first position 74a and the second position 74b may be calculated by the controller 50 and utilized as an input to calculate an estimation of the magnitude and direction of the applied force 30 acting on the elongated probe 14. By monitoring the change in the feature position FP during operation of the imaging system 52, the controller 50 may effectively estimate and document forces and loads applied to the endoscope 12.

Still referring to FIG. 3B, the feature position FP and the principle point PP are both shown as being shifted or translated relative to the center pixel CP in the loaded condition 84. Accordingly, the location of the principle point PP may be monitored to estimate the magnitude of the applied force 30 associated with the loaded condition 84. In such cases, the principle point PP may correspond to a lens feature in the image data utilized to estimate the applied force 30. Similarly, various features (e.g., lens markers, reference datums, identifying serial numbers or text etched on the lens, etc.) that may be indicative of the deflection of the elongated probe 14 may be identified within the image data 20 and tracked to estimate or assist in the estimation of the magnitude of the applied force 30. Further detailed examples of the detection of the feature position FP and change from the first position 74a to the second position 74b are discussed in reference to FIGS. 4A-4D.

In addition to being utilized to identify forces applied to the endoscope 12, the position and/or orientation of one or more of the features may be detected and monitored to support various image processing operations. For example, the location of the principle point PP may be detected by the controller 50 based on the feature position FP and the rotational orientation θ. With this information, the relative position and orientation of the point of distortion (e.g., a hemispherical center, curvature center, defect position, etc.) may be identified and communicated to an image processor or image process controller of the system 52 to assist in the processing and distortion correction of the captured images. For example, the image processor may receive the feature position FP and/or the rotational orientation θ throughout image capture and apply one or more correction, filtering, or other image processing steps based on the relative location of the point of distortion. In this way, the controller 52 may correct or remove distortion, magnification, or scaling associated with the lens and optical properties of the endoscope 12 to improve the presentation of the image data. Accordingly, the disclosure may provide for improvements in image processing as well as the detection of applied forces.

Figure 4B:
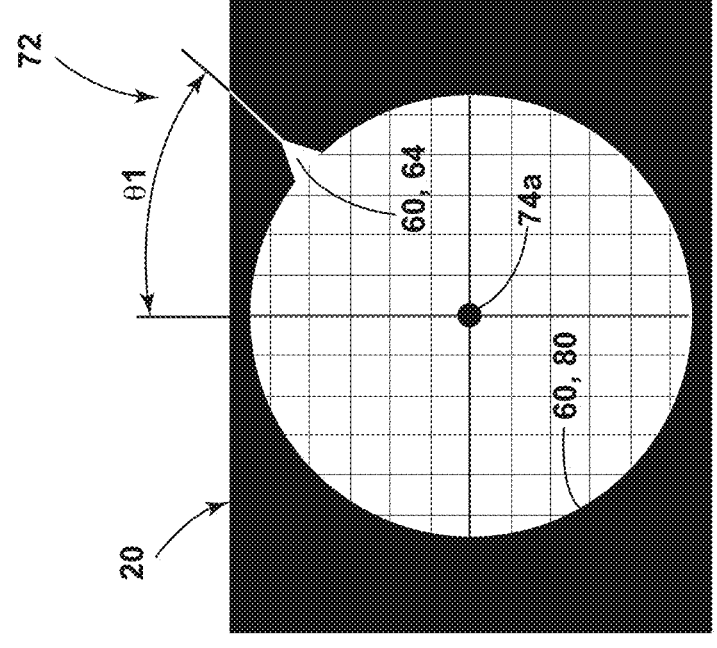
FIG. 4B is a masked schematic representation of image data demonstrating the position of a feature in an undeflected state.
Figure 4A:
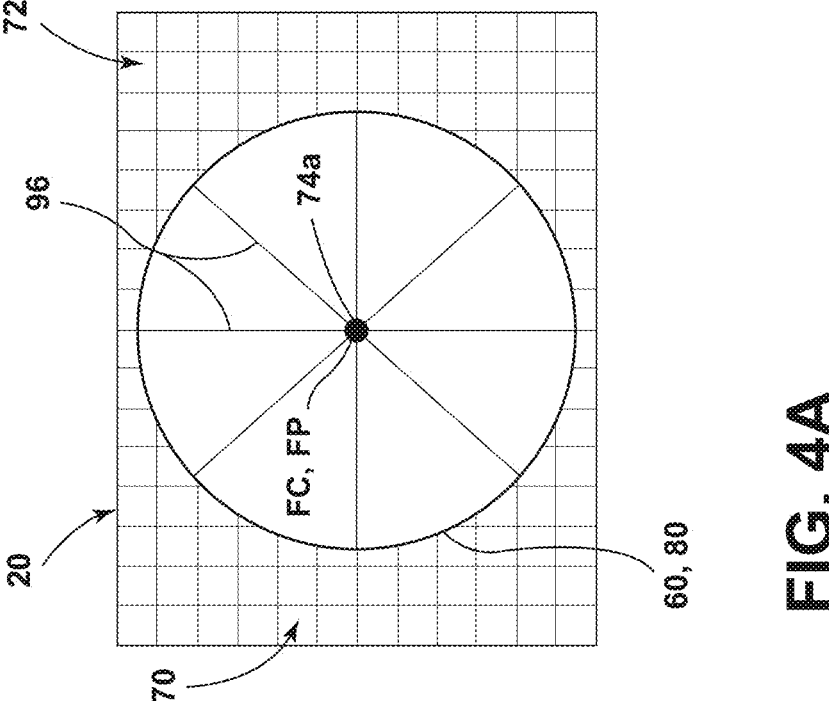
FIG. 4A is an unmasked schematic representation of image data representing the position of a feature in an undeflected state.
Figure 4D:
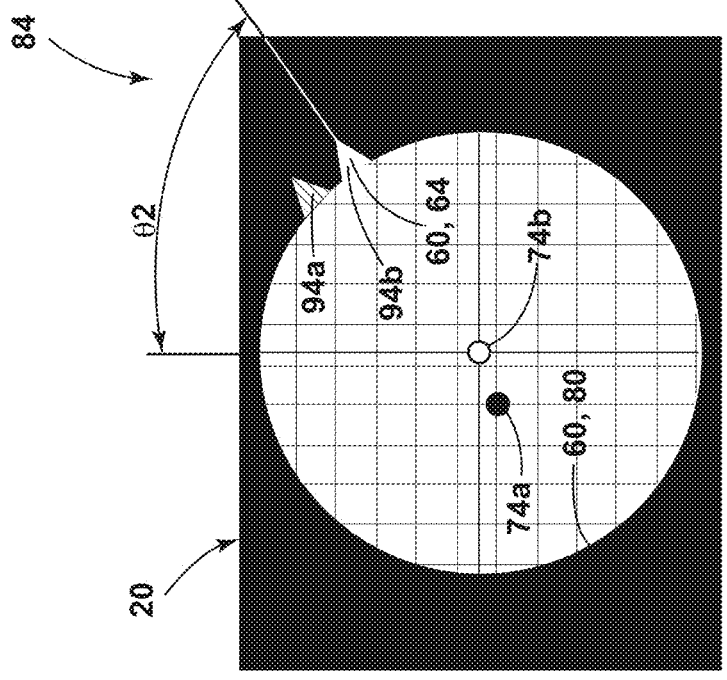
FIG. 4D is a masked schematic representation of image data demonstrating the position of a feature in a deflected state.
Figure 4C:
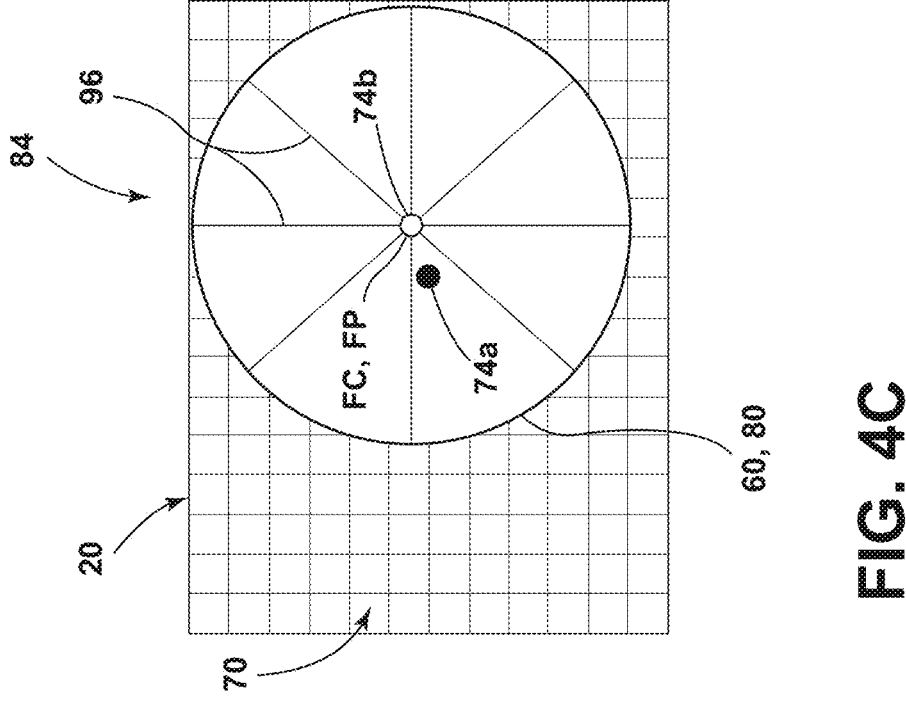
FIG. 4C is an unmasked schematic representation of image data representing the position of a feature in a deflected state.

Referring now to FIG. 4A-4D, schematic representations of the image data are shown demonstrating an exemplary unloaded condition 72 in FIGS. 4A and 4B and an exemplary loaded condition 84 in FIGS. 4C and 4D. FIGS. 4A and 4C demonstrate an inverted image of the field stop mask 62 to assist in describing the detection of the feature position FP based on the perimeter edge 80. FIGS. 4B and 4D demonstrate the identification of a first datum position 94a and a second datum position 94b that may be applied by the controller 50 to determine the rotational orientation θ of the endoscope 12 relative to the camera body 28. As previously discussed, the identification of the rotational orientation θ may assist the imaging system 52 in determining the direction of the applied force and/or isolate the portion of the change in the feature position FP attributed to the deflection 32 from a concurrent change in rotational orientation θ. Accordingly, the example demonstrated in FIGS. 4A-4D may provide for the identification of the first feature position 74a in FIG. 4A and a first rotational orientation θ1 in FIG. 4B in an unloaded condition 72. The calculation of the second feature position 74b is discussed in reference to FIG. 4C, and the calculation of the second rotational orientation θ2 is discussed in reference to a second datum position 94b of the datum 64.

Referring now to FIG. 4A, the first feature position 74a may be identified by detecting the perimeter edge 80 of the field stop mask 62 in the image data 20. As shown, the feature position FP may correspond to the field center FC of the field stop mask 62. The field center FC may be detected by identifying a plurality of points along the perimeter edge 80 and a corresponding intersection of the points passing through the field center FC. The calculation of the field center FC and a corresponding first feature position 74a are demonstrated in FIG. 4A as corresponding to the intersection of a plurality of rays 96 extending perpendicular to the perimeter edge 80. In some cases, a Hough transform may also be utilized to identify the feature position FP as the field center FC. Based on the identification of the first feature position 74a, the controller 50 may assign a reference point for later comparisons of the feature position FP to detect the deflection 32.

In addition to identifying the first feature position 74a, the controller 50 may further identify the rotational orientation θ of the rotational datum 64 or various similar features that may change in position or orientation based on the rotational orientation θ of the endoscope 12 relative to the imager 24. As shown, the rotational orientation θ is positioned in a first rotational orientation θ1. In general, the rotational datum 64 may demarcate and align the rotational orientation θ of the viewing angle 42 of the field of view 22 relative to the instrument axis A. As discussed further in the following examples, the feature position FP may change in response to either the rotation 38 and/or the deflection 32 of the elongated probe 14 to align the alignment axis A relative to the camera body 28. Accordingly, the controller 50 may detect and track changes in the feature position FP as well as the rotational orientation θ to decouple the associated deflection and accurately determine a deflection component of the change in the feature position FP associated with the applied force 30 as well as a rotation component associated with the change in rotational orientation θ.

Referring now to FIG. 4C, the feature position FP is shown translated from the first feature position 74a to the second feature position 74b in the loaded condition 84. For ease of reference, the first feature position 74a is aligned with the center pixel CP of the imager 24. It shall be understood, however, that the first feature position 74a may differ from the location of the center pixel CP and still be detected and tracked throughout the operation of the surgical imaging device 10 to estimate the deflection 32 as a result of the applied force 30. As shown, the feature position FP is shifted laterally and vertically from the first feature position 74a to the second feature position 74b. Additionally, as represented in FIG. 4D, the second datum position 94b is shown oriented at the second rotational orientation θ2. Accordingly, based on the relative location or change in location of the feature position FP from the first feature position 74a to the second feature position 74b as well as the change in the rotational orientation θ from the first rotational orientation θ1 to the second rotational orientation θ2, the controller 50 may estimate the magnitude of the applied force 30 acting on the endoscope throughout operation.

As previously discussed, the change in the feature position FP from the first feature position 74a to the second feature position 74b may be the result of the deflection 32 and/or a change in the rotational orientation θ. The change in the feature position FP associated with the deflection 32 may vary based on the magnitude and/or direction of the applied force 30. The change in the feature position FP may consistently vary in response to the rotational orientation θ of the endoscope 12 relative to the imager 24. Accordingly, in various implementations, the controller 50 may access a lookup table for offset or position information identifying the feature position FP relative to the rotational orientation θ over any entire range of the rotation 38 of the endoscope 12. With this information, the controller 50 may identify the change from the first feature position 74a to the second feature position 74b and calculate the corresponding movement within a pixel array of the imager 24 that is associated with the deflection 32 without a component of the change associated with the change in the rotational orientation θ. For example, by subtracting or factoring out the translational component of the change in the feature position FP associated with the rotational orientation θ, the controller 50 may isolate the translation in the image data 20 and change in the feature position FP associated with the deflection 32. In this way, the controller 50 may isolate and identify changes in the feature position FP associated with a deflection 32 resulting from the applied force 30 acting on the endoscope 12 as opposed to other variables that may influence the feature position FP.

Once the component of the change in the feature position FP associated with the deflection 32 is identified, the applied force 30 may then be estimated by the controller 50. For example, the magnitude of the applied force 30 may be estimated by multiplying a distance of the change or pixel distance associated with the change in the feature position FP by a scalar, a linear equation, or more complex formulas to estimate the force acting on the endoscope 12 throughout operation. It shall be understood by those skilled in art, the equation associated with the estimation of the applied force 30 may vary among different types of endoscopes 12, primarily based on the materials, proportions, and features implemented in the elongated probe. However, the change $\Delta_{FP}$ from the first feature position 74a to the second feature position 74b may correlate to a distance δ of the deflection 32. This relationship may be identified empirically for each device or estimated based on common features that may be implemented in various imaging devices 10. Once the correlation of the change $\Delta_{FP}$ in the feature position FP to the distance δ of the deflection 32, the force may be estimated based on the characteristic stiffness of the endoscope 12, based on static loading calculations. Equation 1 may provide an example of an equation that may be applied to calculate such a force estimate P.

$$P = C_{pixel}\left(\frac{3EI\delta}{L^3}\right) \qquad \text{(Eq. 1)}$$

In the example shown, P is the estimated force and $C_{pixel}$ is a conversion factor between the deflection δ in pixels to a conventional metric measurement scale (e.g., millimeters). E is elastic modulus and I is the area moment of the inertia for the elongated probe 14. Finally, L is the length for the load position or span, which may be approximated as a length 14c of elongated probe. Accordingly, the controller 50 may be programmed to identify the characteristics of the endoscope 12 (e.g., E, I, and L) and estimate the load P based on Equation 1 or similar equations.

Though described in reference to exemplary Equation 1, it shall be understood that the force estimate equation, lookup table, or index utilized to estimate the applied force 30 may be modified to account for a variety of designs of the imaging device 10, particularly in relation to different proportions and features incorporated on the elongated probe 14. For example, in some implementations, the probe 14 may comprise a shaft, a barrel, a sheath, a coupling, an extension, or various elongated portions that may support a lens or optic assembly of the surgical imaging device 10. Additionally, the probe 14 and/or the imaging device 10 may comprise a variety of features including, but not limited to, one or more accessory sheaths, aspiration and/or irrigation lumens, surgical accessories, surgical tools, illumination assemblies, etc. In such cases, the applied force 30 may be estimated for a pixel distance and rotational orientation θ detected in the image data 20 based on one or more equations, scaling factors, look-up tables, etc. that model the behavior of the characteristic stiffness of the imaging device 10 and the elongated probe 14. The relationship of the deflection 32 (δ) and the applied force 30 at the rotational orientation θ may be mapped, measured, and/or modeled in a variety of ways through empirical testing (e.g., load testing in a laboratory), simulations (e.g., finite element analysis), etc. to define the estimated relationship between the deflection 32 (δ) in pixels or image space and the force estimate P for the applied force 30 at the rotational orientation θ.

Figure 5:
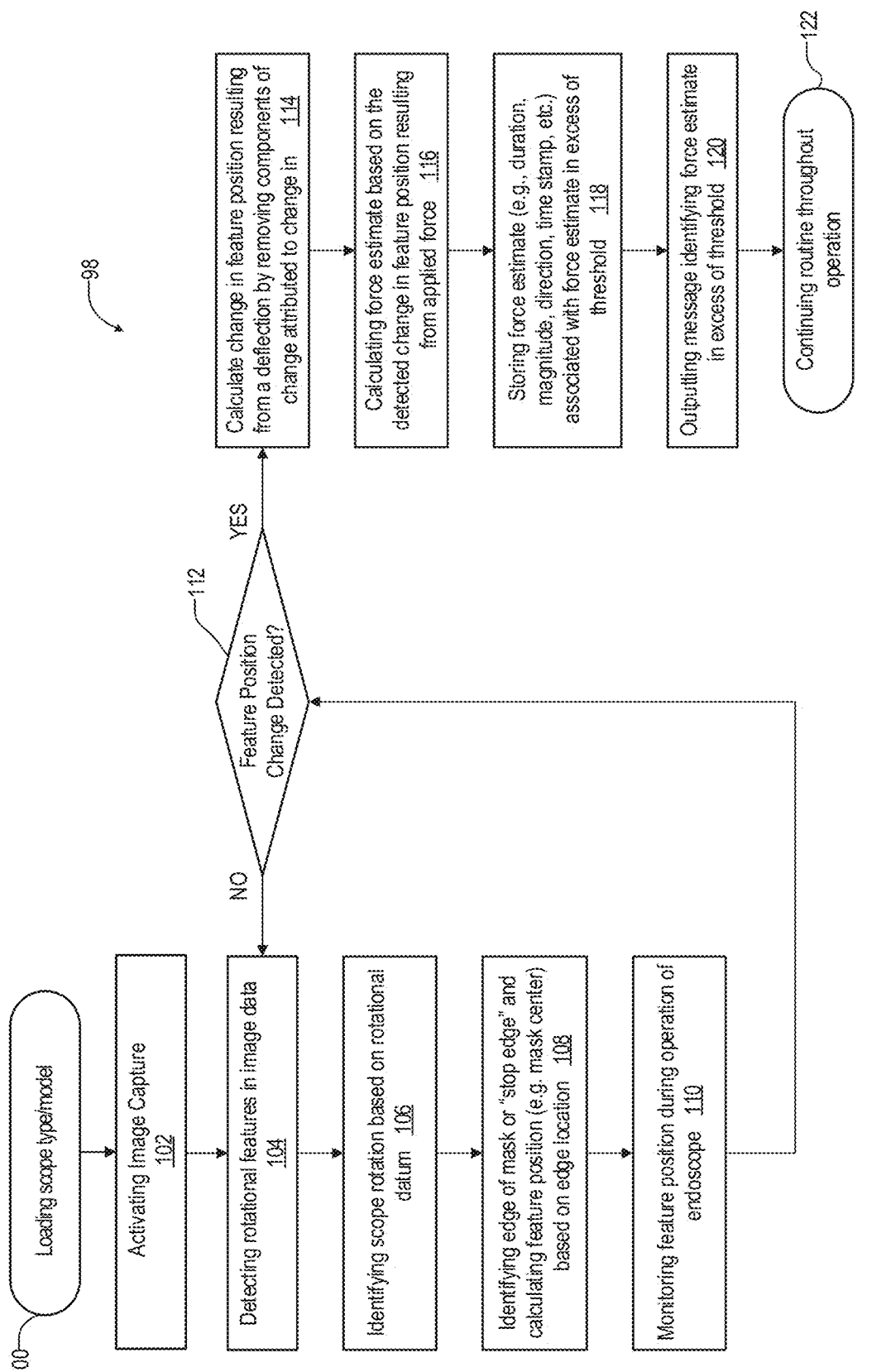
FIG. 5 is a flowchart demonstrating an exemplary method for estimating a force applied to a surgical imaging device based on one or more features detected in image data captured by the imaging device.

Referring now to FIG. 5, a flow chart is shown demonstrating a method 98 for estimating a force applied to an elongated probe 14 of a surgical imaging device 10. In various examples, the method 98 may begin by identifying a model, style, or type of scope connected to the imager 24 or camera body 28 (100). As discussed throughout the application, the system 52 may include an interchangeable scope including the elongated probe 14 with a characteristic stiffness attributed to a variety of physical features and dimensions as previously discussed. Accordingly, the controller 50 may be configured to load or detect the model number, serial number, or more generally, an identification indication of the model or style of the endoscope 12. The identification may be in the form of a user input to a user interface, a communication from the interchangeable scope in the form of a wired or wireless transmission, a feature or model number detected in image data on the field stop mask, the lens, or otherwise visible in the image data. In some examples, the interchangeable scope may comprise a wireless identification transmitter (e.g., a radio frequency identification circuit) that may communicate the identification indication to a receiver of the controller 50. Accordingly, the system 52 may be configured to determine the endoscope 12 and the relationship of the change in position of the feature position FP to the estimation of the applied force 30.

As previously discussed, the method 98 may estimate the applied force 30 based on the image data 20 captured throughout operation of the endoscope 12. Accordingly, the method may begin in response to the activation of the image capture via the imager 24 (102). Once the video feed associated with the image data 20 is activated, the controller 50 may detect one or more feature positions FP or datum positions DP that may be processed to detect and track changes in the rotational orientation θ and the feature position FP. As represented in FIG. 5, step 104 may include the detection of one or more rotational features in the image data 20. As previously discussed, the datum position DP of the rotational datum 64 of the field stop mask 62 may be detected and processed to monitor the datum position DP throughout operation of the imaging device 10. By tracking the datum position DP of the rotational datum 64, the method 98 may continue to identify the scope rotation or rotational orientation θ (106). With the rotational orientation θ identified, the method 98 may continue to detect the change in the feature position FP and isolate the component of the change in the feature position FP that is associated with the deflection 32 from a change associated with the rotational orientation θ. Though discussed in various example, the determination of the rotational orientation θ may be necessary to calculate the force estimation depending primarily on the design of the imaging device 10 (e.g., the rotational coupling 34 and the corresponding alignment of the center point DP with the feature position FP).

As previously discussed, the feature position FP may be detected as a perimeter edge 80 of the field stop mask 62. Once the perimeter edge 80 of the field stop mask 62 is identified, the controller 50 may continue to calculate a mask position, which may correspond to the field center FC or center of the stop mask 62 within the perimeter edge 80 (108). With the feature position FP and the rotational orientation θ identified, the method 98 may monitor the feature position FP for changes in location relative to a center pixel CP or, more generally, based on a location of the feature position FP within a pixel array of the imager 24 (110). In response to a change in the feature position FP, the method may continue to step 114 to calculate a change in the feature position FP resulting from the deflection 32 and corresponding applied force 30 (112). If the change in the feature position FP is not detected, the method may continue to monitor the data position DP and the feature position FP to identify changes that may be attributed to the applied force 30.

As previously discussed and demonstrated in step 114, the change in the feature position FP resulting from the deflection 32 may be distinguished from the changes in the feature position FP that may be the result of change in the rotational orientation θ. Such rotational components associated with the changes in the feature position FP may be subtracted or factored out of the calculation of the changes in the feature position FP by comparing the feature position FP at the determined rotational orientation θ and subtracting the component of the feature position FP associated with the rotational component. In this way, the change in the feature position FP associated with the deflection 32 resulting from the applied force 30 may be distinguished from the changes in the feature position FP that may be associated with changes in the rotational orientation θ. Once the change in the feature position FP associated with the deflection 32 is identified, a force estimate of the applied force 30 may be calculated based on a magnitude of the change in the feature position FP (116). The force estimate may be implemented to support a variety of features related to the operation of the surgical imaging device 10 as well as additional accessories or devices that may be in communication with the imaging system 52.

In step 118, the force estimates calculated by the controller 50 may be stored in a memory or database. For example, in response to a force estimate in excess of a force threshold or predetermined force value, the controller 50 may capture and record a duration, magnitude, direction of deflection, time stamp, date stamp, etc. in memory that may be utilized to document and track force events associated with the use of the surgical imaging device 10. Additionally, in some cases, the controller 50 may output a message to a user interface or display that may be associated with the surgical imaging device 10 and/or various systems that may be in communication with the imaging system 52 that may identify a force estimate or force detection in excess of a force threshold (120). In addition to the message identifying the force estimate in excess of the threshold, controller 50 may also activate one or more alarms, notifications, and/or status messages that may be output to a user interface of the imaging system 52 and/or various controllers, computers, servers, and/or accessories that may be in communication with the imaging device 10. Finally, as demonstrated in step 122, the method 98 may continue throughout operation of the surgical imaging device 10. Corresponding notifications may be communicated to alert or notify surgeons or users of the system 52 of events or activity related to the detection of the applied force 30.

Figure 6:
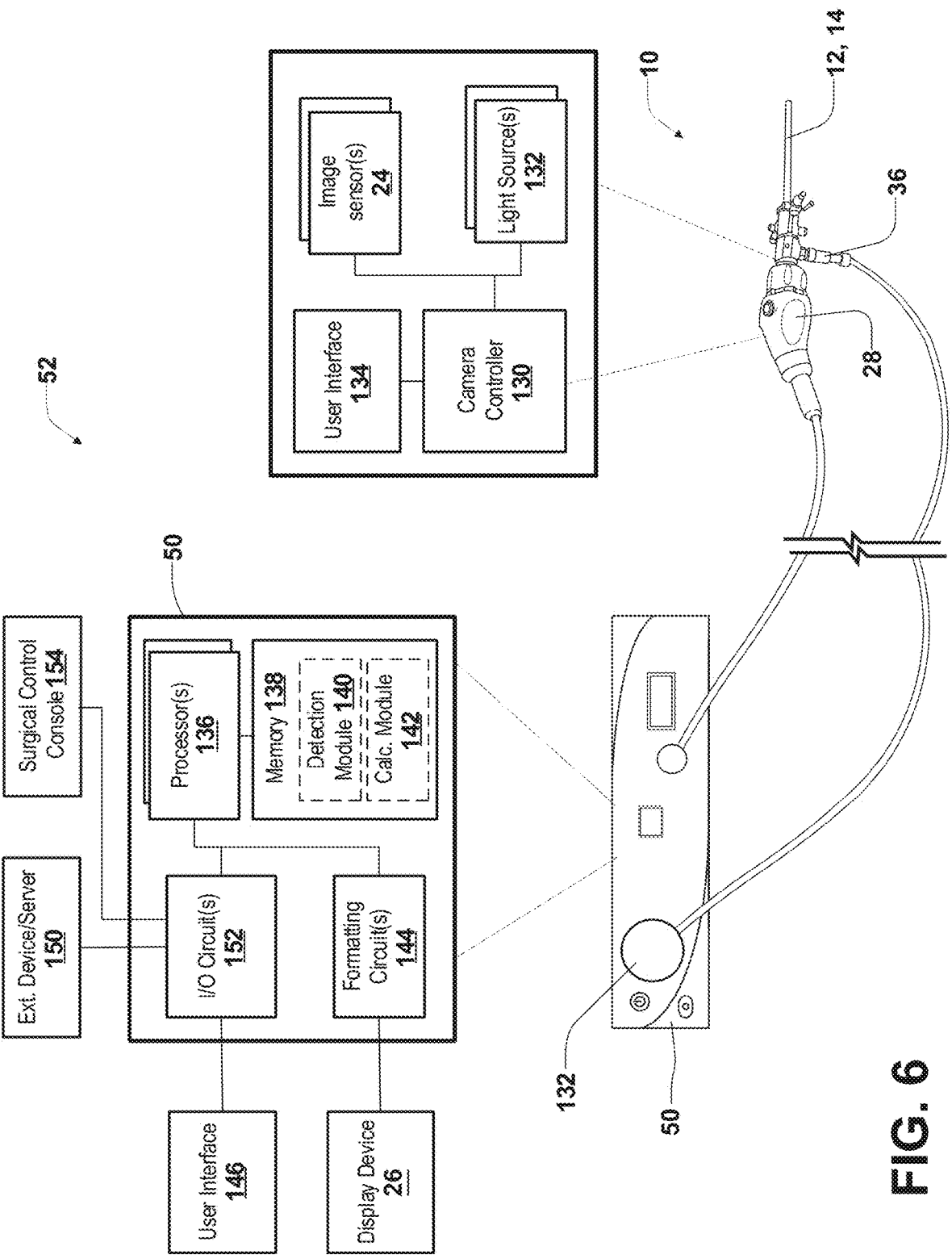
FIG. 6 is a block diagram demonstrating an exemplary surgical imaging device and display controller in accordance with the disclosure.

Referring now to FIG. 6, a block diagram of the imaging system 52 is shown. As discussed throughout the disclosure, the system 52 may comprise the imaging device 10 in communication with the controller 50. The imaging device 10 may comprise a light source 132, the imager 24, a camera controller 130, and a user interface 134. In various implementations, the imaging device 10 may correspond to an endoscope, laparoscope, arthroscope, etc. with the elongated probe 14 comprising a narrow distal end 14b suited to various noninvasive surgical techniques. For example, the distal end 14b may include a diameter of less than 2 mm. As demonstrated, the imaging device 10 may be in communication with the controller 50 via communication interface. Though shown connected via a conductive connection, the communication interface may correspond to a wireless communication interface operating via one or more wireless communication protocols (e.g., Wi-Fi, 802.11 b/g/n, etc.).

The light source 132 may correspond to various light emitters configured to generate light in the visible range and/or the near infrared range. In various implementations, the light source 132 may include light emitting diodes (LEDs), laser diodes, or other lighting technologies. The imager 24 or image sensor may correspond to various sensors and configurations comprising, for example, charge-coupled devices (CCD) sensors, complementary metal-oxide semiconductor (CMOS) sensors, or similar sensor technologies. As previously discussed, the system 52 and particularly the controller 50 may process or compare the image data to detect one or more features 60 that may be associated with the endoscope 12. Once detected, the positions of the one or more features 60 may be monitored to identify changes that are not associated with the native operation of the imaging device 10. Changes that may be native to the operation of the imaging device 10 may include changes in the position of the features 60 attributed to changes in the rotational orientation of the endoscope 12 relative to the imager 24 or camera body 28. Once the native changes associated with the operation of the imaging device 10 are identified, the changes in the feature position FP associated with an applied force 30 may be isolated to estimate a force applied to the endoscope 12. In this way, the disclosure may provide for the detection of forces applied to the endoscope 12 of the imaging device 10.

In various implementations, the camera controller 130 may correspond to a control circuit configured to control the operation of imager 24 and the light source 132 as well as process and/or communicate the image data 20 to the controller 50 or system controller. Additionally, the camera controller 130 may be in communication with a user interface 134, which may include one or more input devices, indicators, displays, etc. The user interface 134 may provide for the control of the imaging device 10 including the activation of one or more routines as discussed herein. The camera controller 130 may be implemented by various forms of controllers, microcontrollers, application-specific integrated controllers (ASICs), and/or various control circuits or combinations.

The controller 50 or system controller may comprise a processor 136 and a memory 138. The processor 136 may include one or more digital processing devices including, for example, a central processing unit (CPU) with one or more processing cores, a graphics processing unit (GPU), digital signal processors (DSPs), field programmable gate arrays (FPGAs), application specific integrated circuits (ASICs) and the like. In some configurations multiple processing devices are combined into a System on a Chip (SoC) configuration while in other configurations the processing devices may correspond to discrete components. In operation, the processor 136 executes program instructions stored in the memory 138 to perform the operations described herein.

The memory 138 may comprise one or more data storage devices including, for example, magnetic or solid state drives and random access memory (RAM) devices that store digital data. The memory 138 may include one or more stored program instructions, object detection templates, image processing algorithms, etc. As shown, the memory 138 may comprise a detection module 140 and a calculation module 142. The detection module 140 may include instructions to process the image data identifying the features 60 (e.g., the field stop mask 62, rotational datum 64, etc.) in the image data 20. The detection module 140 may further be configured to monitor and track the feature position FP as well as the datum position DP through operation of the imaging system 52. For example, the processor 136 may access instructions in the detection module 140 to perform various processing tasks on the image data including pre-processing, filtering, masking, cropping, and various enhancement techniques to improve detection capability and efficiency. Additionally, the detection module 140 may provide instructions to process various feature detection tasks including template matching, character recognition, feature identification or matching, etc. In some examples, the detection module 140 may also include various trained models for object detection and/or identifying the features 60 in the image data 20.

The calculation module 142 may be configured to calculate the force estimation based on the rotational orientation $\theta$ and the feature position FP or change in the feature position identified by the controller 50. As previously discussed, the controller 50 may be configured to apply the detected rotational orientation $\theta$ to isolate the deflection component of the change in the feature position FP resulting from the applied force 30 from the rotational component resulting from the rotational orientation $\theta$. As previously discussed, the controller 50 may access a database, lookup table, offset equation, or calibration data identifying a relative location of the feature position FP over the operating range of the rotational orientation $\theta$ (e.g., 360 degrees). Accordingly, at each temporal instance of the force calculation and corresponding detection of the feature position FP and the rotational orientation θ, the controller 50 may adjust or subtract the offset associated with the rotational orientation θ from the feature position FP in order to consistently identify and compare the feature position FP isolated or decoupled from the changes associated with the variation in the rotational orientation θ.

Once the rotational component is removed or otherwise accounted for from the change in the feature position FP, the remaining change in the feature position FP may be associated with the deflection 32 resulting from the applied force 30. Accordingly, the filtered or isolated change in the feature position FP associated with deflection may be multiplied by a scalar value, input into a linear or non-linear equation, or otherwise converted from a pixel distance similar displacement value to a corresponding force estimate of the applied force 30 acting on the endoscope 12. The force estimate conversion from the change in position detected in the image data (e.g., the pixel distance) to the force estimate may be calculated based on the characteristic stiffness associated with the length, stiffness, material type, shaft thickness, or various other characteristics that may be associated with the model, style, type, or various features of the endoscope 12 and the camera body 28. Additionally, the calculations and equations associated with the force estimation may necessarily depend on the type of imager 24 (e.g., resolution, pixel array proportions, etc.). Finally, in some cases, the characteristic stiffness of the endoscope 12 may also vary based on the rotational orientation θ of the endoscope 12 relative to the imager 24 and the camera body 28. In some cases, the stiffness of the endoscope 12 may vary based on the rotational orientation θ due to features that vary along the length 14c of the shaft of the endoscope 12 (e.g., a light position, stiffening features, etc.). Accordingly, the calculation and associated equations may vary based on the model, style, and/or type of the endoscope 12, camera body 28, and/or imager 24. However, the corresponding relationship of the force estimation corresponding to the deflection 32 and the detected change in the feature position FP may be determined empirically for each combination and saved to the memory 138 to ensure that the force estimation can be accurately assessed for a variety of applications.

As previously described, the nature of the equation applied to calculate the force estimate may correspond to a scalar modifier, a linear equation or a non-linear equation, which may comprise inputs identifying the change in the feature position FP and the rotational orientation θ. The nature of the force estimate equation may primarily be based on the deflection response of the endoscope 12 as a result of the applied force. For example, the magnitude of the displacement may not correlate linearly to the magnitude of the applied force 30 due to the response of the deflection 32 along the length 14c of the endoscope 12. The deflection 32 may vary based on the structural features of the endoscope 12 and the material, as well as the structural stability of the rotational coupling 34. Accordingly, the force estimation equation may vary considerably depending on the specific combination of the endoscope 12, imager 24, and the camera body 28. However, as previously discussed, the relationship of the displacement of the feature position FP in the image data 20 may, in response to a range of magnitudes of the applied force 30 and the rotational orientation θ, be empirically tested by the manufacturer and calibrated to ensure that the force estimate may be accurately calculated for a variety of surgical imaging devices.

As previously discussed, in some implementations, the controller 50 may correspond to a display controller. In such applications, the controller 50 may include one or more formatting circuits 144, which may process the image data received from the imaging device 10, communicate with the processor 136, and process the image data according to one or more of the operating methods discussed herein. The formatting circuits 144 may include one or more signal processing circuits, analog-to-digital converters, digital-to-analog converters, etc. The display controller may comprise a user interface 146, which may be in the form of an integrated interface (e.g., a touchscreen, input buttons, an electronic display, etc.) or may be implemented by one or more connected input devices (e.g., a tablet) or peripheral devices (e.g., keyboard, mouse, etc.).

As shown, the controller 50 is also in communication with an external device or server 150, which may correspond to a network, local or cloud-based server, device hub, central controller, or various devices that may be in communication with the controller 50 and, more generally, the imaging system 52 via one or more wired (e.g., Ethernet) or wireless communication (e.g., Wi-Fi, 802.11 b/g/n, etc.) protocols. For example, the controller 50 may receive updates to the various modules and routines as well as communicate sample image data from the imaging device 10 to a remote server for improved operation, diagnostics, and updates to the imaging system 52. The user interface 146, the external server 150, and/or the surgical control console 154 may be in communication with the controller 50 via one or more I/O circuits 152. The I/O circuits 152 may support various communication protocols including, but not limited to, Ethernet/IP, TCP/IP, Universal Serial Bus, Profibus, Profinet, Modbus, serial communications, etc.

According to some aspects of the disclosure, a method is provided for detecting an applied force to a surgical imaging device comprising an elongated probe extending from a proximal body. The method further comprises capturing image data in a field of view, detecting a feature in the image data, and in response to a feature location of the feature in the image data, assigning a first position to the feature. The method may then continue by monitoring the feature location of the feature in the image data, detecting a change in the feature location of the feature from the first position to a second position, and in response to the change in the feature location of the feature to the second position, calculating a force estimate applied to the elongated probe.

According to various aspects, the method may implement one or more of the following features or various combinations of the features:

the feature is a component of the surgical imaging device captured in the field of view;

the feature is a perimeter mask forming a perimeter edge about a central portion of the image data defining a viewing area;

the feature location is calculated by detecting a mask position of the perimeter mask within the field of view;

detecting the perimeter edge of a viewing area defined by the perimeter mask;

calculating a mask center of the perimeter mask by identifying an intersection of a plurality of points about the perimeter edge, wherein the mask center identifies the mask position;

the feature comprises at least one locating datum depicted in the image data;

detecting a datum position of the locating datum in the field of view;

identifying a rotational orientation of the elongated probe in response to the datum position of the locating datum in the image data;

adjusting the calculation of the force estimate based on the rotational orientation of the elongated probe;

the calculation of the force estimate is adjusted by adjusting the calculation for a drift in the feature location from the change from the first position to the second position, wherein the drift is attributed to a predetermined change in the feature location associated with the rotational orientation;

comparing the force estimate to a predetermined threshold, and in response to the force estimate exceeding the predetermined threshold, outputting notification message identify excessive force applied to the elongated probe; and recording the force estimate and a time of a corresponding force event in a memory in communication with the surgical imaging device.

According to another aspect of this disclosure, a surgical imaging apparatus is provided comprising an imager configured to capture image data in a field of view. An elongated probe extends from a proximal end to a distal end, wherein the distal end includes a distal window through which the field of view is aligned. A controller is in communication with the imager and is configured to detect a feature in the image data, identify a feature location of the feature in the image data, monitor the feature location in the image data, and in response to a change in the feature location from a first position to a second position, calculate a force applied to the elongated probe.

According to various aspects, the apparatus may implement one or more of the following features or various combinations of the features:

the imager is disposed in a housing in connection with the proximal end portion of the elongated probe, wherein the elongated probe is connected to the housing via a rotational coupling;

the controller is configured identify a rotational orientation of the elongated probe relative to the imager in response to a datum location of a datum identified in the image data;

the controller is configured to adjust the calculation of the force estimate based on the rotational orientation of the elongated probe;

the calculation of the force estimate is adjusted by correcting for a shift in the feature location, wherein the shift is attributed to a predetermined change in the feature location of the feature associated with the rotational orientation;

the calculation of the force estimate is adjusted based on a predetermined directional rigidity of the elongated probe relative to the rotational orientation;

the controller is configured to identify a positional offset of the feature location in the image data in response to a rotation of the elongated probe over at least a portion of a rotational range of the elongated probe relative to the imager.

the feature is a perimeter mask forming a perimeter edge about a central portion of the image data defining a viewing area in the field of view;

the controller is configured to detect a perimeter edge of a viewing area defined by the perimeter mask; and calculate a mask center of the perimeter mask, wherein the mask center identifies the mask position.

According to still further aspects of the disclosure, a surgical imaging apparatus is provided including an imager configured to capture image data in a field of view and disposed in a housing. An elongated probe extends from the housing from a proximal end to a distal end, wherein the distal end comprises a distal window through which the field of view is aligned. The elongated probe is connected to the housing via a rotational coupling. A controller is in communication with the imager. The controller is configured to detect a feature in the image data, identify a feature location of the feature in the image data, determine a rotational orientation of the elongated probe relative to the imager in response to a datum location of a datum identified in the image data, monitor the feature location and the datum location in the image data, and in response to a change in the feature location from a first position to a second position, calculate a force applied to the elongated probe. The calculation of the force accounts for a portion of the change in the feature location associated with the rotational orientation based on the datum location.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

The invention claimed is:

1. A method for detecting an applied force to a surgical imaging device comprising an elongated probe through which a field of view is captured, the elongated probe extending from a proximal body, the method comprising:

capturing image data in the field of view of the surgical imaging device;

detecting a feature in the image data;

in response to a feature location of the feature in the image data, assigning a first position to the feature;

monitoring the feature location of the feature in the image data;

detecting a change in the feature location of the feature from the first position to a second position; and in response to the change in the feature location of the feature to the second position, calculating a force estimate applied to the elongated probe, wherein the force estimate identifies a lateral deflection of the elongated probe.

2. The method according to claim 1, wherein the feature is a component of the surgical imaging device captured in the field of view.

3. The method according to claim 1, wherein the feature is a perimeter mask forming a perimeter edge about a central portion of the image data defining a viewing area.

4. The method according to claim 3, wherein the feature location is calculated by detecting a mask position of the perimeter mask within the field of view.

5. The method according to claim 4, further comprising:

detecting the perimeter edge of a viewing area defined by the perimeter mask; and calculating a mask center of the perimeter mask by identifying an intersection of a plurality of points about the perimeter edge, wherein the mask center identifies the mask position.

6. The method according to claim 1, wherein the feature comprises at least one locating datum depicted in the image data; and the method further comprising:

detecting a datum position of the locating datum in the field of view.

7. The method according to claim 6, further comprising:

identifying a rotational orientation of the elongated probe in response to the datum position of the locating datum in the image data.

8. The method according to claim 7, further comprising:

adjusting the calculation of the force estimate based on the rotational orientation of the elongated probe.

9. The method according to claim 8, wherein the calculation of the force estimate is adjusted by adjusting the calculation for a drift in the feature location from the change from the first position to the second position, wherein the drift is attributed to a predetermined change in the feature location associated with the rotational orientation.

10. The method according to claim 1, further comprising:

comparing the force estimate to a predetermined threshold; and in response to the force estimate exceeding the predetermined threshold, outputting a notification message to identify excessive force applied to the elongated probe.

11. The method according to claim 1, further comprising:

recording the force estimate and a time of a corresponding force event in a memory in communication with the surgical imaging device.

12. A surgical imaging apparatus comprising:

an imager configured to capture image data in a field of view;

an elongated probe extending from a proximal end to a distal end, wherein the distal end comprises a distal window through which the field of view is aligned; and a controller in communication with the imager, the controller configured to:

detect a feature in the image data;

identify a feature location of the feature in the image data;

monitor the feature location in the image data; and in response to a change in the feature location from a first position to a second position, calculate a lateral force applied to the elongated probe.

13. The apparatus according to claim 12, wherein the imager is disposed in a housing in connection with the proximal end portion of the elongated probe, wherein the elongated probe is connected to the housing via a rotational coupling.

14. The apparatus according to claim 12, wherein the controller is further configured to:

identify a rotational orientation of the elongated probe relative to the imager in response to a datum location of a datum identified in the image data.

15. The apparatus according to claim 14, wherein the controller is further configured to:

adjust the calculation of the lateral force estimate based on the rotational orientation of the elongated probe.

16. The apparatus according to claim 15, wherein the calculation of the lateral force estimate is adjusted by correcting for a shift in the feature location, wherein the shift is attributed to a predetermined change in the feature location of the feature associated with the rotational orientation.

17. The apparatus according to claim 15, wherein the calculation of the lateral force estimate is adjusted based on a predetermined directional rigidity of the elongated probe relative to the rotational orientation.

18. The apparatus according to claim 12, wherein the controller is further configured to:

identify a positional offset of the feature location in the image data in response to a rotation of the elongated probe over at least a portion of a rotational range of the elongated probe relative to the imager.

19. The apparatus according to claim 12, wherein the feature is a perimeter mask forming a perimeter edge about a central portion of the image data defining a viewing area in the field of view, and wherein the controller is further configured to:

detect a perimeter edge of a viewing area defined by the perimeter mask; and calculate a mask center of the perimeter mask, wherein the mask center identifies the mask position.

20. A surgical imaging apparatus comprising:

an imager configured to capture image data in a field of view and disposed in a housing;

an elongated probe extending from the housing from a proximal end to a distal end, wherein the distal end comprises a distal window through which the field of view is aligned, wherein the elongated probe is connected to the housing via a rotational coupling; and a controller in communication with the imager, the controller configured to:

detect a feature in the image data;

identify a feature location of the feature in the image data;

determine a rotational orientation of the elongated probe relative to the imager in response to a datum location of a datum identified in the image data;

monitor the feature location and the datum location in the image data; and in response to a change in the feature location from a first position to a second position, calculate a force applied to the elongated probe, wherein the calculation of the force accounts for a portion of the change in the feature location associated with the rotational orientation based on the datum location.

* * * * *